United States Patent [19]

Frant et al.

[11] 4,267,023

[45] May 12, 1981

[54] CHEMICALLY INTEGRATING DOSIMETER AND GAS ANALYSIS METHODS

[75] Inventors: Martin S. Frant, Newton; Jon Soderberg, East Falmouth, both of Mass.

[73] Assignee: Orion Research Incorporated, Cambridge, Mass.

[21] Appl. No.: 96,572

[22] Filed: Nov. 21, 1979

Related U.S. Application Data

[63] Continuation-in-part of Ser. No. 842,394, Oct. 17, 1977, abandoned.

[51] Int. Cl.³ .................... G01N 27/46; G01N 27/56
[52] U.S. Cl. .................... 204/1 T; 23/232 R; 23/232 E; 73/23; 204/195 P; 422/83; 422/88; 422/98
[58] Field of Search ........... 204/1 F, 1 H, 1 P, 195 P; 422/83, 88, 98; 23/232 R, 232 E; 73/23

[56] References Cited

U.S. PATENT DOCUMENTS

| | | | |
|---|---|---|---|
| 3,098,813 | 7/1963 | Beebe et al. | 204/195 P |
| 3,227,643 | 1/1966 | Okun et al. | 204/195 P |
| 3,278,408 | 10/1966 | Leonard et al. | 204/195 P |
| 3,357,908 | 12/1967 | Riseman et al. | 204/195 P |
| 3,574,078 | 4/1971 | Hynes et al. | 204/195 P |
| 3,575,836 | 4/1971 | Sternberg | 204/195 P |
| 3,622,488 | 11/1971 | Chand et al. | 204/195 P |
| 3,649,505 | 3/1972 | Strickler et al. | 204/195 P |
| 3,668,101 | 6/1972 | Bergman | 204/195 P |
| 3,718,546 | 2/1973 | Salzano et al. | 204/1 F |
| 3,718,563 | 2/1973 | Krull et al. | 204/195 P |
| 3,730,868 | 5/1973 | Niedrach | 204/195 P |
| 3,756,923 | 9/1973 | Dahms | 204/195 P |
| 3,767,552 | 10/1973 | Laurer | 204/195 P |
| 3,787,308 | 1/1974 | Malaspina et al. | 204/195 P |
| 3,803,006 | 4/1974 | Kreuger et al. | 204/195 P |
| 3,830,709 | 8/1974 | Kreuger et al. | 204/195 P |
| 3,830,718 | 8/1974 | Riseman et al. | 204/195 P |
| 3,847,777 | 11/1974 | Haddad et al. | 204/195 P |
| 3,979,274 | 9/1976 | Newman | 204/195 P |
| 3,992,153 | 11/1976 | Ferber et al. | 23/232 R |
| 4,132,616 | 1/1979 | Tantram et al. | 204/195 P |

OTHER PUBLICATIONS

Reiszner et al., "Environmental Sciences & Technology", vol. 7, No. 6, Jun. 1973, pp. 526-532.

Primary Examiner—G. L. Kaplan
Attorney, Agent, or Firm—John B. Miller

[57] ABSTRACT

A chemically integrating dosimeter for measuring gases, composed of a dual membrane system and an internal electrolyte solution. The outer membrane is a gas permeation rate controlling membrane. The inner membrane is a microporous hydrophobic protective membrane interposed between the electrolyte solution and the outer membrane. The dosimeter makes accurate determinations of time integrated exposures to various gases in the atmosphere and can be conveniently used by workers in industrial environments over a wide range of field conditions.

47 Claims, 1 Drawing Figure

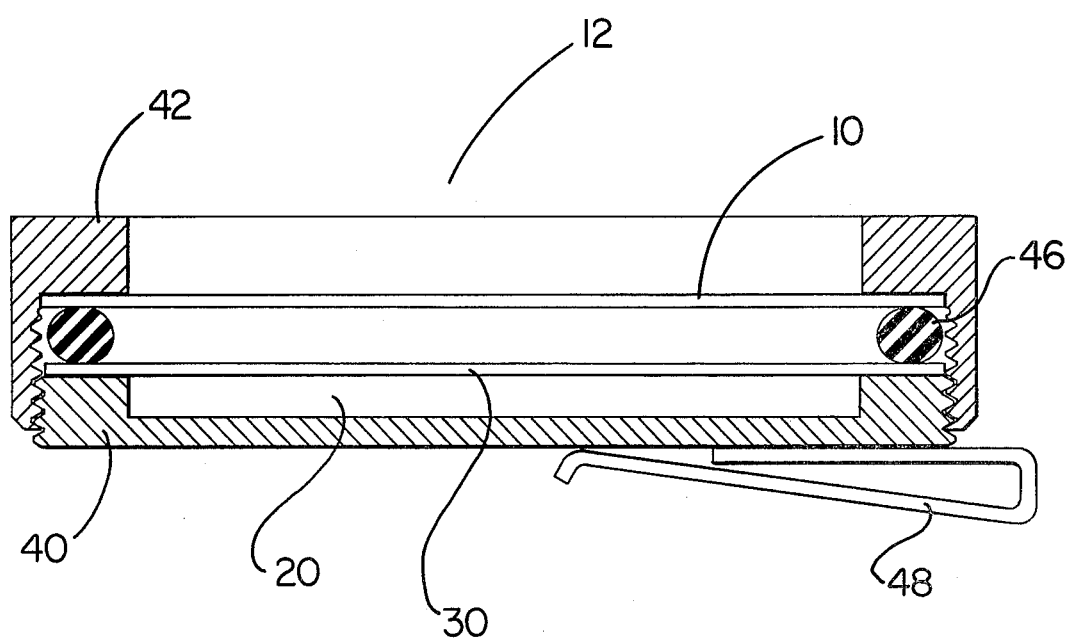

CHEMICALLY INTEGRATING DOSIMETER AND GAS ANALYSIS METHODS

This is a continuation-in-part of Ser. No. 842,394 filed Oct. 17, 1977 and now abandoned.

BACKGROUND OF THE INVENTION

1. Field of Invention

This invention relates to the detection of various gases in the atmosphere, and more specifically to measuring time weighted exposures of those gases with a chemically integrating dosimeter.

2. Prior Art Statement

High sensitivity determinations of various gases in the workroom atmosphere have been made necessary by the establishment of federal standards for industrial air. See, Federal Register, Vol. 36, No. 105, May 29, 1971. Although a wide variety of methods has been proposed and used for the determination of the many gases subject to these federal standards, the present invention relates specifically to the measurement of the following gases in workroom air at atmospheric pressures: hydrogen sulfide, $H_2S$; sulfur dioxide, $SO_2$; hydrogen chloride, HCl; ammonia, $NH_3$; hydrogen fluoride, HF; and hydrogen cyanide, HCN. The presence of these gases in sufficient quantities in industrial air can be injurious to human health. For example, hydrogen sulfide, $H_2S$, is a toxic contaminant often encountered in the industrial processing of gas and gas streams. Exposure to $H_2S$ gas in even small amounts can result in olfactory paralysis in less than fifteen minutes. Longer periods of exposure result in sickness and death. See, Hydrocarbon Processing & Petroleum Refiner 42:115, April, 1963. Sulfur dioxide gas, $SO_2$, is a major source of atmospheric pollution. Because of its corrosive and poisonous characteristics, sulfur dioxide is an extremely dangerous pollutant. The gas causes irritation and inflammation of the eyes and respiratory paralysis if present in sufficient concentration. Concentrations of approximately 1 ppm are believed injurious to plant life.

Threshold limit values (TLV), i.e., the time weighted average for maximum allowable exposure over an eight-hour day or a forty-hour week, have been prescribed for each of the gases listed above. See, "TLV's for Chemical Substances in Workroom Air," adopted by American Conference of Governmental Industrial Hygienists (ACGIH) for 1976. In particular, the current threshold limit value (TLV) for $H_2S$ is 10 parts per million (ppm). Exposures up to 15 ppm are permissible for $H_2S$ if the time weighted average remains below the TLV of 10 ppm. The current threshold limit value (TLV) for $SO_2$ and HCl is 5 parts per million (ppm). Short term exposure is also limited to 5 ppm. The current TLV for ammonia, $NH_3$, is 25 ppm. Short term exposure is limited to 35 ppm. The TLV for hydrogen cyanide, HCN, is 10 ppm, with allowable short term exposure at 15 ppm. The TLV for hydrogen fluoride, HF, is 3 ppm, with short term exposure also at 3 ppm.

Since these federal regulations require the measurement of time weighted exposure of workers to gases, techniques which make cumulative, i.e., time integrated, determinations of gas concentrations are desirable. Devices which measure concentrations at a particular instant are inconvenient since repeated measurements, followed by arithmetic integration, are required to arrive at a cumulative exposure value. Even devices which continually measure gas concentrations are limited by the need for arithmetic integration of results over time. Arithmetic integration of a series of measurements at specific time intervals is misleading if the interval between measurements is large enough that variations in gas concentrations are not detected. The expense of frequent measurements, coupled with the requirements for time integrated exposures, illustrates the limitations of present systems for determining long term exposure to gases.

One such present system, a means for measuring hydrogen sulfide gas, has been disclosed by Riseman, et al, and described in U.S. Pat. No. 3,915,831. A hydrogen sulfide, $H_2S$, sensing cell uses a sulfide-ion sensitive electrode, in conjunction with a reference electrode. The permeation of $H_2S$ across a single membrane into a reference solution is determined by potentiometrically measuring the change in sulfide ion concentration in the solution.

One "Method of Determining Sulfur Dioxide and Sensing Cell Therefor" has been disclosed by Kreuger, Frant, and Riseman in U.S. Pat. No. 3,803,006. The method uses a hydrogen ion sensitive glass electrode in conjunction with a Ag/AgCl reference electrode. $SO_2$ permeates across a single membrane into an aqueous solution of sulfite or bisulfite salt, where the $SO_2$ dissolves and reacts with $H^+$ ion to form sulfite and bisulfite ions. $SO_2$ is determined by potentiometrically measuring the change in $H^+$ ion concentration.

Chand has disclosed an apparatus for measuring sulfur dioxide in U.S. Pat. No. 3,622,488. $SO_2$ permeates across a single semipermeable membrane into a dilute sulfuric acid electrolyte. Electro-oxidation of sulfur dioxide to $SO_4^{-2}$ occurs at a noble metal sensing electrode, and generated current is measured between this electrode and a counter-electrode. While $SO_2$ concentration is thereby determined, the device does not measure time integrated exposure to $SO_2$.

Reiszner and West describe a method for Determination of Sulfur Dioxide in "Environmental Science & Technology," Vol. 7, No. 6, p. 526, June 1973. $SO_2$ gas permeates through a single gas permeable membrane into a sodium tetrachloromercurate (II) internal solution, forming the stable dichlorosulfitomercuate (II) complex. The dichlorosulfitomercurate (II) complex is extremely sensitive to direct sunlight and must be protected from solar radiation through the use of a light-shield mounting box. $SO_2$ concentration is then determined by the lengthy and complex West-Gaeke procedure, described in ASTM 02914-70 T.

A measuring cell for determining the concentration of $SO_2$ in a fluid has been disclosed by Dahms in U.S. Pat. No. 3,756,923. The cell includes an electrode covered with a thin layer of an electrolyte containing silver ions, and a counter electrode. When a voltage is applied across the electrodes, the resulting current is a measure of the concentration of $SO_2$. In one of its forms, the electrolyte is separated from the sample fluid by means of a single membrane, composed of silicon rubber of polytetrafluorethylene. Disposed between the membrane and the electrolyte can be a porous spacer which is ion permeable and wettable. The function of the porous spacer is to provide a geometrically well-defined layer of electrolyte on the electrode. The cell does not make time integrated measurements of $SO_2$ gas.

A sulfur oxide meter for measuring changes in $SO_2$ activity directly in an electrochemical cell has been disclosed by Salzano, et al, in U.S. Pat. No. 3,718,546. Both a reference and a sample oxygen bearing electrode are exposed to a fused salt electrolyte. One or more membranes which are porous to a cation common to the electrolyte are used to isolate the reference and sample gas electrodes from each other. The $SO_2$ activity is determined by measuring the output electromotive force (EMF) of the cell, which is a function of the difference in activities between the $SO_2$ in the reference gas and that in the test sample. The device For measurements of ammonia, $NH_3$, an electrode has been disclosed by Riseman, et al, in U.S. Pat. No. 3,830,718. The standard electrolyte solution comprises a saturated aqueous solution of an ammonium salt of a strong acid having a pK of not more than 3, the salt having an aqueous solubility at room temperature such that the ammonium ion concentration is about 0.001 M to 1 M. A single microporous hydrophobic membrane with a porosity sufficiently great so as to readily pass ammonia gas but not great enough to permit any appreciable passage of liquid or ions, separates the electrolyte from the sample gas. The electrode provides real time, but not integrated, determinations of ammonia concentrations.

An ammonia sensor has been disclosed by A. Strickler, et al, in U.S. Pat. No. 3,649,505. An electrochemical cell comprises a hydrogen ion sensitive electrode and a reference electrode joined by an ammonium-ion containing electrolyte. The electrodes and electrolyte are separated from the sample being analyzed by a single microporous hydrophobic membrane, highly permeable to ammonia gas and substantially impermeable to liquid and ions. In a preferred form, a second inner hydrophilic membrane is interposed between the first membrane and the internal electrolyte. The second membrane is ion permeable and may be composed of very thin cellophane or filter paper. The inner membrane ensures that an electrolyte film is provided between the outer membrane and the ion sensitive electrode.

A dosimeter for measuring nitrogen dioxide has been disclosed by Ferber, et al, in U.S. Pat. No. 3,992,153, which makes arithmetically determined time weighted average measurements of $NO_2$. The nitrogen oxide to be measured passes through a single, gas-permeable, liquid-impermeable membrane into an internal gas-absorbing solution. The rate of entry of gas molecules into the absorbing solution is controlled by the permeability of the membrane and by the concentration of the ambient gases. The gas molecules stoichiometrically react with the internal solution to form $NO_3^-$ ion. The change in $NO_3^-$ concentration is monitored with an ion sensor and the ambient $NO_2$ gas concentration can be back calculated. Ferber also discloses the use of a glass-fiber filter impregnated with acidic sodium dichromate to convert NO to $NO_2$ by oxidation. In this manner, exposure to NO can be determined. This filter is disposed externally to the membrane.

A gas-sensing electrochemical cell for measuring nitrogen dioxide dissolved in a sample solution has been disclosed by Kreuger, et al, in U.S. Pat. No. 3,830,709. The cell comprises a potentiometric hydrogen ion-sensitive electrode and a reference electrode, both in contact with an internal standard solution comprising an aqueous acid solution of a nitrite salt. A single hydrophobic gas permeable membrane separates the sample solution from the internal solution. The cell does not make time integrated measurements of $NO_2$ gas.

Several other techniques for the general measurement of atmospheric gases have been disclosed in the art. For example, a polarographic sensor for measuring atmospheric gases, composed of a pair of electrodes joined by an electrolyte has been disclosed by Krull, et at, in U.S. Pat. No. 3,718,563. A multi-layer gas permeable, essentially ion impermeable membrane separates the electrodes and the electrolyte from the sample medium. The outer layer of the membrane is preferably formed of silicone rubber. The inner layer is formed of a material less permeable to gas and water vapor than the outer membrane.

Two other patents which relate to applicant's invention are described below. An electrochemical gas analyzer is disclosed by Laurer in U.S. Pat. No. 3,767,552. The anode and cathode are in contact with each other by means of an internal electrolyte. Separating the two electrodes is a disc, permeable to liquids but impermeable to solids, which prevents particles of the anode from contacting the cathode. A gas-permeable, liquid impermeable membrane separates the electrodes and the electrolyte from the sample to be analyzed. A second flexible, liquid impermeable expansion membrane is disposed internally to both the electrolyte and the electrodes.

An electrolytic sensor to measure carbon dioxide, $CO_2$, with water diffusion compensation has been disclosed by Riseman, et al, in U.S. Pat. No. 3,357,907. A single membrane selectively permeable to gases separates an electrochemically active sample species from an electrode which is sensitive to an ionic concentration in an internal electrolyte placed between the electrode and the membrane. This ionic concentration is a fundtion of the concentration of the sample species. In one form of the invention, spacing means, such as a cellophane film, is disposed internally to the membrane. The spacing means is permeable to gases and water, and is wettable.

SUMMARY OF INVENTION

The present invention contemplates a chemically integrating dosimeter, composed of a dual membrane system and an internal electrolyte solution wherein the outer membrane is a gas permeation rate controlling membrane and the inner membrane is a microporous hydrophobic protective membrane. The inner membrane is interposed between the outer membrane and the internal electrolyte solution. The object of the invention is to provide a small, simple, and lightweight dosimeter with long shelf life that makes high sensitivity time weighted average determinations of gases in the atmosphere such as, but not limited to: hydrogen sulfide, $H_2S$; sulfur dioxide, $SO_2$; hydrogen chloride, HCl; ammonia, $NH_3$, hydrogen flouride, HF; and hydrogen cyanide, HCN.

The dosimeter is comprised of an outer and inner membrane and an electrolyte solution disposed internally to the inner membrane. The outer membrane is composed of a material substantially liquid impermeable. This material is selected so that the permeation rate of the gas species to be measured is significantly slower than the diffusion rate of the same gas species in air. The inner protective membrane is hydrophobic and microporous, as well as liquid water impermeable. It serves two purposes, the first of which is to protect the outer membrane from direct chemical attack by the internal electrolyte. The second purpose is to essentially eliminate precipitate formation and/or deposition on the outer membrane and hence any effect on its permeability. While precipitates may be deposited on the inner membrane, the pores of the membrane are large enough to preclude any but long term changes in the effective permeability rate of the inner membrane.

The chemical composition of the internal electrolyte is selected so that upon entry of the gas to be measured a chemical reaction occurs between said gas and the electrolyte such that the concentration of the gas is brought to zero within the electrolyte. At the same time this reaction also causes a change in the concentration of a selected ion. By electrochemically measuring the change in concentration of the selected ion, the amount of the gas entering the dosimeter during the exposure period is determined.

BRIEF DESCRIPTION OF THE DRAWINGS

For a more full understanding of the nature and objects of the invention, reference should be made to the following detailed description taken in connection with the accompanying drawing wherein a diagrammatic, side-elevational, cross-sectional view of a preferred from of the present invention is shown.

DETAILED DESCRIPTION OF THE INVENTION

In the drawing, the two membrane dosimeter is depicted as comprising an outer membrane 10, and inner membrane 30, through which ambient gas species 12 permeates. Outer membrane 10 is physically separated from inner membrane 30 by O-ring 46; in other examples, they can be in direct physical contact. The placement of both is made secure through the use of structural base 40, and annularly mounted cap 42. Clip 48 is used to attach the dosimeter to clothing. Electrolyte 20 is disposed internally to inner membrane 30.

The gas species 12 to be measured by the dosimeter permeate through the outer membrane 10, through the inner membrane 30, and are absorbed in internal electrolyte 20. By the term "absorbed" used here and in the claims it is meant that a chemical reaction occurs between the gas to be measured and the electrolyte such that (a) the concentration of the gas in the electrolyte is brought to zero and (b) the concentration of a selected ion within the electrolyte is altered. By measuring the change in concentration of the ion, the amount of gas absorbed can be determined. The dosimeter is therefore chemically integrating in the sense that the reaction within the electrolyte begins upon exposure to the gas to be measured and continues throughout the exposure period. An integrated total concentration for exposure period is measured. As will appear more fully herein, the dual membrane structure can be used in the determination of i.e., the following gases in the atmosphere: hydrogen sulfide, $H_2S$; sulfur dioxide, $SO_2$; hydrogen chloride, $HCl$; ammonia, $NH_3$; hydrogen fluoride, $HF$; and hydrogen cyanide, $HCN$.

Outer membrane 10 is composed of material substantially permeable to gases and substantially impermeable to liquids. Silicone rubber and sillicone polycarbonate copolymer are examples of suitable membrane materials. Liquid permeable membranes could also be used but as these can be subject to wetting and have varying gas permeability rates, liquid impermeable membranes are preferred. The inner membrane 30 is substantially ion-impermeable, hydrophobic and liquid water impermeable. It is composed of a substantially non-reactive microporous material, such as microporous polytetrafluorethylene or copolymers of tetrafluorethylene and hexafluoropropylene in weight ratio of approximately 95:5 to 75:25 (available as Teflon ®, a registered trademark of E. I. duPont de Nemours and Co., Inc.), microporous polyvinylchloride, microporous polyvinylfluoride, microporous polyethylene, and microporous polypropylene.

There are qualitative limits to the maximum and minimum allowable values for outer membrane permeability. If permeability is too low, the rate of gas absorption will be below the limit of detection. If permeability is too high, the rate of gas absorption affects the gas concentration outside the membrane, making it sensitive to the rate and direction of air movement. These "windage" effects are precluded when the permeation rate of gas species through the outer membrane is significantly lower than the diffusion rate of the same gas species in air. The permeability of the inner membrane is preferably selected to be at least four times greater than that of the outer membrane. This ensures that it is the permeability of the outer membrane that controls the rate of gas molecule entry into internal electrolyte 20.

The dual membrane system effectively eliminates two experimental difficulties encountered in the use of single membrane chemically integrating dosimeters. The first of these is the deposit of precipitate resulting from the absorption of gas 12 in the electrolyte 20. This deposition causes a change in membrane permeability during exposure. The interposition of the inner membrane 30, which is hydrophobic and ion-impermeable, prevents the precipitate from depositing on the rate controlling outer membrane 10. At the same time, precipitation on the inner protective membrane does not interfere with the operation of the dosimeter as its pores are sufficiently large to preclude any but long term effects on the permeability rate. The second experimental difficulty arises when the internal electrolyte selected to react with the absorbed gas is chemically reactive with the gas permeation membrane. The interposition of the non-reactive inner membrane 30 between electrolyte 20 and the rate controlling membrane 10 overcomes the chemical attack problem.

As used in the claims, the inner membrane 30 is a "protective" membrane in two senses. First, the microporous hydrophobic nature of the inner membrane prevents any changes in the gas permeation rate through the inner membrane due to precipitate formation within the electrolyte 20. This is due to the air-gap nature of these materials which contain very little structure in relation to the volume of holes or gaps. Precipitation that does occur upon entry of the gas into the electrolyte is on the surface of the structure of the inner membrane and not on the gaps, and thus does not effect permeation rate.

The inner membrane is also "protective" in the sense that the inner membrane's liquid impermeable nature prevents the electrolyte 20 from entering the gaps in the membrane and therefore from contacting the outer membrane 10. Chemical reaction (or attack) between the electrolyte 20 and outer membrane 10 is prevented, protecting the gas permeation rate of the outer membrane at both short and long-term intervals. Shelf-life of the dosimeter is extended since no interaction can occur between the gas permeation rate controlling outer membrane and the electrolyte. Regardless of the chemical reaction which occurs within the electrolyte, the permeability of the gas of interest through the outer membrane remains unaffected.

As an example of how the two membrane dosimeter prevents precipitate deposition on the outer membrane 10, the hydrogen sulfide, $H_2S$, dosimeter is more fully described. The composition of internal electrolyte 20 is selected to be at a convenient concentration of, for example, $7.0 \times 10^{-4}$ M $AgNO_3$ in 1 M $Na_4$ EDTA (ethylene di-nitrilo tetracetate ion), silver complexing agent, adjusted to a pH of 12. Upon permeation of gas species 12 into internal electrolyte 20, the following two reactions occur:

$$H_2S \text{ (gas)} + 2OH^- \rightleftharpoons 2H_2O + S^{-2} \quad (1)$$

$$2Ag^+ + S^{-2} \rightleftharpoons Ag_2S \text{ precipitate} \quad (2)$$

Exposure to $H_2S$ is determined by measing the decrease in concentration of $Ag^+$ ion resulting from the precipitation of silver sulfide. Upon contacting the electrolyte, $H_2S$ gas is completely converted to sulfide ion $S^{-2}$ and bisulfide ion $HS^-$. While some of the precipitate may deposit on the inner protective membrane 30, this action has no adverse effect on the membrane's permeability due to its microporous nature. The decrease in $Ag^+$ ion concentration can be monitored by a combination $Ag/S$ electrode, (Model #941600, available from Orion Research Incorporated, Cambridge, Mass.).

The selection of a suitable $Ag^+$ ion concentration for internal electrolyte 20 is based on the following equation $$V_g = \frac{P \cdot t \cdot A(H \cdot \Delta p)}{KT} \quad (3)$$

where:
$V_g$ is the volume of absorbed $H_2S$ at room temperature and pressure, in cubic centimeters,
P is the permeability of the outer membrane,
K is a constant equal to $1 \times 10^9$,
T is the thickness of the outer membrane in cm.,
t is the absorption time in seconds,
A is the area of the outer membrane in square centimeters,
$(H \cdot \Delta p)$ is the design partial pressure for $H_2S$, where H is the height of mercury at standard pressure in centimeters, and
$\Delta p$ is the TLV for hydrogen sulfide gas, times $10^{-6}$.
A silicon rubber polycarbonate copolymer (MEM 213, available from General Electric Co., Schenectady, N.Y.) is selected for the outer membrane. It is $2.54 \times 10^{-3}$ cm thick, 6.0 square centimeters in area, and has a permeability P of 220. The height of mercury is 76.0 cm and the $\Delta P$ is $10 \times 10^{-6}$. For an eight-hour day, absorption time is $2.88 \times 10^4$ seconds.

Solving for $V_g$, the volume of $H_2S$ absorbed in an eight-hour day is determined to be $1.14 \times 10^{-2}$ cm$^3$. If a dosimeter with 4 ml of internal solution is used, the concentration of absorbed $H_2S$ in that 4 ml of solution is $1.27 \times 10^{-4}$ M. Since two $Ag^+$ ions are consumed for each $H_2S$ molecule absorbed in producing $Ag_2S$, the silver ion concentration in the internal electrolyte must be at least twice the concentration of absorbed $H_2S$, or $2.54 \times 10^{-4}$ M. The method of measurement is subtractive in the sense that a final $Ag^+$ ion concentration is subtracted from an initial $Ag^+$ ion concentration. Tests with this method indicate that the most precise results are obtained when the final concentration is roughly half that of the initial. For this reason, initial $Ag^+$ ion concentration is again doubled to $5.08 \times 10^{-4}$ M. The $AgNO_3$ concentration of $7.0 \times 10^{-4}$ M is chosen to be slightly greater than this design value.

One of the advantages of the electrolyte utilized for determining $H_2S$ is that interferences from halogen ions, such as $Cl^-$, and from HCl, can be eliminated by the addition of an appropriate silver complex of such strength that sulfide reacts with silver present in the complex as readily as with free silver ion. Other silver complexing agents which maintain a free silver activity between $10^{-6}$ and $10^{-17}$ may be used in place of $Na_4$ EDTA. Since silver chloride is relatively much more soluble than silver sulfide, it will not be precipitated in the presence of the complex.

By way of illustration, for silver chloride to precipitate and thereby interfere with $H_2S$ measurement, the product of the silver ion activity and the chloride ion activity must be greater than the $K_{sp}$, which is $10^{-9.2}$.

$$(Ag^+)(Cl^-) > K_{sp} \quad (4)$$

In the presence of EDTA the siliver ion activity is given by equation 5.

where $\beta$ is the literature value of the stability constant for EDTA which is $10^{7.3}$, and R is the total silver concentration.

By solving equation (5) for $(Ag^+)$, substituting in equation (4), then solving for $(Cl^-)$, equation (6) is obtained.

$$(Cl^-) > (K_{sp})(EDTA)(\beta)/R \quad (6)$$

Tests were conducted near the pK for EDTA, at pH = 12.0. Roughly half of the EDTA present is active. For the $7.0 \times 10^{-4}$ $AgNO_3$ in 1 M $Na_4$ EDTA solution, the minumum chloride concentration required for precipitation can be determined.

$$(Cl^-) > 24.50/(2) > 12.25 \text{ M} \quad (7)$$

where 2 is a correction factor for active EDTA. Only at excessively high chloride concentrations will chloride ion interfere. The concentration of active EDTA can be chosen to preclude any anticipated chloride ion interference. Given an anticipated concentration of chloride ion and the above equation, an EDTA concentration can be selected to eliminate any interference. In this case, HCl or $Cl_2$ at 10 times the ACGIH TLV values of 5 ppm and 3 ppm, respectively, do not interfere.

TABLES I and II illustrate the success of the two-membrane structure over the conventional one-membrane system utilized in the past in maintaining the effective permeability of the outer membrane. A silicon rubber outer membrane and a microporous Teflon ® inner membrane were used. Internal electrolyte 20 was a silver complex of $7 \times 10^{-4}$ M $AgNO_3$ in 1 M $Na_4$ EDTA (adjusted to pH=12.0). Even at lower levels of $H_2S$, TABLE I indicates the $Ag_2S$ precipitate alters effective permeability of the silicon rubber single membrane to render such a system ineffective. The 10 hour tests show a measured drop of 13.7 ppm from the known supply of 25 ppm of $H_2S$. TABLE II shows the increased accuracy resulting from the use of the double membrane structure. "Average $H_2S$ Concentration" was found to be very close to "Generated $H_2S$ Concentration".

TABLE I

SINGLE MEMBRANE DOSIMETER
Long Term Exposure to H₂S

| Time of Run | No. of dosimeters tested | Generated H₂S Concn. | Average H₂S Concn. found | % Error |
|---|---|---|---|---|
| 10 hrs. | 7 | 25 ppm | 11.3 ppm/hr | 54.8 |
| 6 hrs. | 8 | 25 ppm | 22.3 ppm/hr | 10.8 |
| 5 hrs. | 6 | 25 ppm | 19.8 ppm/hr | 20.8 |
| 4 hrs. | 6 | 25 ppm | 25.6 ppm/hr | 2.4 |
| 4 hrs. | 8 | 25 ppm | 24.0 ppm/hr | 4.0 |
| 1 hr. | 8 | 25 ppm | 25.0 ppm/hr | 0.0 |

TABLE II

DOUBLE MEMBRANE DOSIMETER
Long Term Exposure to H₂S

| Time of Run | No. of dosimeters tested | Generated H₂S concn. | Average H₂S Concn. found | % Error |
|---|---|---|---|---|
| 7 hrs. | 4 | 25 ppm | 24.7 ppm/hr | 1.2 |
| 7 hrs. | 4 | 25 ppm | 25.3 ppm/hr | 1.2 |
| 7 hrs. | 8 | 25 ppm | 25.6 ppm/hr | 2.4 |
| 7 hrs. | 8 | 30 ppm | 30.0 ppm/hr | 0.0 |
| 6 hrs. | 5 | 40 ppm | 38.1 ppm/hr | 4.8 |

Test results show the reliable determinations of H₂S in the 5-32 ppm range can be made for durations up to an eight-hour work day. Threshold limit values have been set by the ACGIH in 1976 at 10 ppm for time weighted average and 15 ppm for short term exposure limit. The dosimeter has an observed shelf life of over eight months.

In an analogous dosimeter for hydrogen chloride, HCl, the internal electrolyte 20 is a silver nitrate solution, $AgNO_3$. Upon absorption of HCl, silver chloride precipitate is formed according to equation 8. ($K_{sp} = 1.8 \times 10^{-10}$).

$$HCl + Ag^+ + NO_3^- \rightleftharpoons AgCl_{ppt.} + HNO_3 \tag{8}$$

The decrease in $Ag^+$ ion concentration is measured with a silver/sulfide electrode (Model #941600, available from Orion Research Incorporated, Cambridge, Mass.). The interposition of the inner membrane protects the outer diffusion rate controlling membrane from precipitate deposition. A second benefit is that the inner membrane also prevents silver ion from being absorbed into the silicone rubber or polycarbonate copolymer outer membrane, thereby altering the permeability of the outer membrane. As an example of the selection of a suitable silver nitrate, $AgNO_3$, concentration, a dual membrane dosimeter having an outer membrane with a permeability constant P of 500, $2.54 \times 10^{-3}$ cm thick, area of 6 square centimeters and 1 ml of internal electrolyte is considered. At the TLV of 5 ppm (7 mg/cubic meter) per eight-hour day, HCl would enter the solution at $1.84 \times 10^{-11}$ moles/second, and the internal solution would be about $5 \times 10^{-4}$ M after eight hours. Since the silver ion concentration must exceed the expected HCl level, a minimum $Ag^+$ ion concentration of $10^{-3}$ M would be used.

Similarly, in a dual membrane dosimeter for measuring hydrogen fluoride, HF, the internal electrolyte 20 is a calcium acetate solution, $Ca(OAc)_2$. Upon absorption of HF, calcium fluoride precipitate is formed according to equation 9 ($K_{sp} = 1.8 \times 10^{-11}$).

$$2HF + Ca^{+2} + 2(OAc)^- \rightleftharpoons CaF_2\ ppt. + 2HOAc \tag{9}$$

The decrease in $Ca^{+2}$ concentration is measured with a calcium electrode (Model #922001, available from Orion Research Incorporated, Cambridge, Mass.). The interposition of the inner protective membrane 30 prevents the deposition of calcium fluoride precipitate on the outer membrane. For a dual membrane dosimeter with an outer membrane $2.54 \times 10^{-3}$ cm thick, an area of 6 square centimeters, an internal electrolyte volume of 1 ml and a permeability constant P of 400, a minimum $Ca(OAc)_2$ concentration of $2.5 \times 10^{-4}$ M is used to measure HF at the TLV range of 3 ppm for an eight-hour day.

As an example of how the dual membrane dosimeter eliminates chemical attack on the gas permeation membrane, said dosimeter for measuring sulfur dioxide, $SO_2$, is more fully described. In the $SO_2$ dosimeter, the composition of internal electrolyte 20 is conveniently selected to be $1 \times 10^{-3}$ M mercuric bromide ($HgBr_2$) in $5 \times 10^{-3}$ M acetic acid buffer (HOAc/NaOAc) at pH 4.8 with 1% dimethylformamide. Upon permeation of gas species 12 into internal solution 20, the following reactions occur.

$$SO_2\ (gas) + H_2O \rightleftharpoons 2H^+ + SO_3^{-2} \tag{10}$$

$$HgBr_2 + SO_3^{-2} \rightleftharpoons Hg(SO_3)Br^- + Br^- \tag{11}$$

$$Hg(SO_3)Br^- + SO_3^{-2} \rightleftharpoons Hg(SO_3)2^{-2} + Br^- \tag{12}$$

Exposure to $SO_2$ is determined by measuring the increase in concentration of $Br^-$ ion.

Experimentation indicates that in addition to reaction (12) above, the mercuric sulfite-bromide complex also reacts with mercuric bromide in solution to form sulfate ion, $SO_4^{-2}$, mercurous bromide precipitate, and bromide ion, according to equation (13).

$$Hg(SO_3)Br^{-1} + HgBr_2 + H_2O \rightarrow SO_4^{-2} + Hg_2Br_2\ ppt. + Br^- + 2H^+ \tag{13}$$

Free energy calculations indicate that the above reaction is possible, although the time for complete reaction at room temperature is on the order of one week. Heating the dosimeter at 90° C. for 10-15 minutes completes reaction 13 above and stabilizes the $Br^-$ ion concentration. The $Br^-$ ion determination can thereafter be made at convenience, since heating does not change the amount of $SO_2$ absorbed. Accuracy of determination does not depend on the time at which the heating occurs. The increase in $Br^-$ ion concentration is measured with a bromide electrode (Model #943500, available from Orion Research Incorporated, Cambridge, Mass.).

The gas permeation membrane is susceptible to chemical attack by the mercuric bromide/acetic acid complex. By interposing the liquid impermeable inner membrane 30 between the outer membrane and the electrolyte attack by the internal electrolyte 20 on the outer membrane 10 is prevented. The selection of a suitable mercuric bromide concentration for internal solution 20 is governed by the analysis already described for H₂S and shown in equation 3. For the same geometry dosimeter as in the H₂S case, with a permeability P of 80 and a $\Delta p$ of $5 \times 10^{-6}$, the volume of $SO_2$ absorbed in an eight-hour day is $2.05 \times 10^{-3}$ cm³. The concentration of absorbed $SO_2$ is $1.16 \times 10^{-2}$ M.

One of the added advantages of the electrolyte utilized for $SO_2$ measurement is that the presence of ammonia, hydrogen chloride, and chlorine, does not interfere. The major interference with $SO_2$ determinations is $H_2S$, which quantitatively forms mercuric sulfide and also liberates bromide. For most applications, however, this is not a problem in that usually only one species or the other is present. Using an internal electrolyte wherein the number of moles of bromide ion is in the range between one and ten times the number of moles of the highest level of $SO_2$ to be measured, reliable determinations of $SO_2$ in the 0.5–50 ppm range can be made for durations up to an eight-hour day.

In a dosimeter analogous to the $SO_2$ dosimeter, ammonia, $NH_3$, can be measured using a very dilute mercuric chloride complex as internal electrolyte 20. The mercuric chloride complex is undissociated and is present as a covalent compound with very little free chloride present. In the presence of ammonia a new complex with mercury is formed, and chloride ion, $Cl^-$, is released, according to equation 14. (Stability constant $= 1.8 \times 10^9$).

$$HgCl_2 + 4NH_3 \rightleftharpoons Hg(NH_3)_4^{+2} + 2Cl^-$$

The increase in $Cl^-$ ion concentration is measured with a chloride electrode (Model #941700, available from Orion Research Incorporated, Cambridge, Mass.). Since the outer membrane is susceptible to chemical attack by the mercuric chloride complex and absorption of the complex into said membrane, the interposition of the inner protective membrane insulates the outer membrane from both of these adverse effects. The selection of a suitable mercuric chloride complex concentration is governed by the same analysis shown for $H_2S$ in equation 3. For the same geometry dosimeter as in the $H_2S$ case with a permeability P of 1500 and a $\Delta P$ of $50 \times 10^{-6}$, the rate of $NH_3$ entry is $5.5 \times 10^{-10}$ moles/sec. After 8 hours of exposure the 1 ml internal solution would be about $1.5 \times 10^{-2}$ M $NH_3$. Since the ratio of mercuric chloride reacting is one atom of mercury to four molecules of ammonia, a minimum $HgCl_2$ concentration of $7.5 \times 10^{-3}$ M would be used.

Similarly, in a dual membrane dosimeter for measuring hydrogen cyanide, HCN, the internal electrolyte 20 contains an argentocyanide complex, which dissociates to a small but measurable degree to form silver ion and cyanide ion, as shown in equation 15. Stability constant $= 1.0 \times 10^{21}$.

$$Ag(CN)_2^- \rightleftharpoons Ag^+ + 2CN^-. \qquad (15)$$

When hydrogen cyanide gas, HCN, is absorbed by the internal electrolyte, additional $CN^-$ ion is provided and equilibrium equation (15) is forced toward the left. The decrease in $Ag^+$ ion concentration is measured with a silver/sulfide electrode (Model #941600, available from Orion Research Incorporated, Cambridge, Mass.). Hydrogen cyanide exposure is thereby determined. The argentocyanide complex electrolyte solution 20 is insulated from the outer membrane 10 by inner protective membrane 30, eliminating any chemical attack by the complex on said outer membrane. The argentocyanide complex is used as an indicator only, and a convenient minimum concentration is $10^{-4}$ M $Ag^+$. For a permeability P of 900, $\Delta p = 10 \times 10^{-6}$, an outer membrane thickness of $2.54 \times 10^{-3}$ cm, and 1 ml of internal solution 20, the rate of HCN gas entry is $6.6 \times 10^{-11}$ moles/sec. After eight hours exposure, the concentration of HCN is $1.9 \times 10^{-3}$ M.

What is claimed is:

1. Method for detecting hydrogen sulfide gas by chemical integration comprising the steps of:
   providing a gas permeable, liquid impermeable outer membrane in conjunction with a liquid impermeable microporous hydrophobic inner membrane, the latter with a gas permeation rate substantially greater than that of the outer membrane;
   placing an internal electrolyte solution containing silver ions in contact with the inner membrane;
   allowing hydrogen sulfide gas to diffuse through the outer membrane, through the inner membrane, and into the internal electrolyte where the outer membrane is a gas permeation rate controlling membrane, and the inner membrane is a protective membrane;
   reacting the internal electrolyte with hydrogen sulfide gas to completely absorb said gas and to alter the composition of the internal electrolyte; and
   measuring the change in the concentration of silver ions in the electrolyte due to the entry of hydrogen sulfide gas into the internal electrolyte, whereby the concentration of the gas is determined.

2. The method of claim 1 wherein the internal electrolyte contains a silver ion concentration buffered with a silver complexing agent.

3. The method of claim 2 wherein the number of moles of $Ag^+$ ion in the internal electrolyte is in the range between two and four times the number of moles of the highest level of $H_2S$ to be detected, said highest level to be four times the threshold limit value of 10 ppm.

4. The method of claim 2 wherein the internal electrolyte is $7 \times 10^{-4}$ M $AgNO_3$.

5. The method of claim 2 wherein the silver complexing agent is $Na_4EDTA$.

6. The method of claim 5 wherein the concentration of $Na_4$ EDTA is 1 M.

7. The method of claim 2, wherein the silver complexing agent is a solution in a concentration which maintains a free silver activity in the electrolyte between $10^{-6}$ and $10^{-17}$.

8. The method of claim 1 wherein the outer membrane is silicone polycarbonate copolymer.

9. The method of claim 1 wherein the inner membrane is microporous polytetrafluoroethylene.

10. The method of claim 1 wherein the outer membrane is silicone rubber.

11. The method of claim 1 wherein the inner membrane is microporous polyvinylchloride.

12. The method of claim 1 wherein the inner membrane is microporous polyvinylfluoride.

13. The method of claim 1 wherein the inner membrane is polypropylene.

14. The method of claim 1 wherein the inner membrane is microporous polyethylene.

15. A chemically integrating dosimeter for measuring hydrogen sulfide gas in the atmosphere comprising:
   a structural base, open on one side, for housing a solution;
   an internal electrolyte solution containing silver ions and a complexing agent, placed in the structural base so that upon absorption of $H_2S$ gas into the electrolyte a chemical reaction occurs within the electrolyte causing a change in silver ion concentration;
   a gas permeable, liquid impermeable gas permeation rate-controlling outer membrane with a permeation rate for $H_2S$ gas substantially lower than the diffusion rate of H₂S gas in air, placed to cover the opening in the structural base;

a microporous hydrophobic inner membrane substantially more permeable to gases than the outer membrane, impermeable to the internal electrolyte, and interposed between the internal electrolyte solution and the outer membrane to prevent chemical attack on the outer membrane by the electrolyte and to prevent precipitate deposition from the electrolyte on the outer membrane;

means to seal the inner membrane and the outer membrane to the structural base; and means to measure the change in concentration of silver ions $Ag^+$ in the internal electrolyte.

16. The dosimeter of claim 15 wherein the outer membrane is silicone rubber.

17. The dosimeter of claim 15 wherein the outer membrane is silicone polycarbonate copolymer.

18. The dosimeter of claim 15 wherein the inner membrane is microporous polytetrafluoroethylene.

19. The dosimeter of claim 15 wherein the inner membrane is microporous polyvinylchloride.

20. The dosimeter of claim 15 wherein the inner membrane is microporous polyethylene.

21. The dosimeter of claim 15 wherein the inner membrane is microporous polyvinylfluoride.

22. The dosimeter of claim 15 wherein the inner membrane is microporous polypropylene.

23. The dosimeter of claim 15 wherein the internal electrolyte is silver nitrate.

24. The dosimeter of claim 15 wherein the silver complexing agent is a solution in a concentration which maintains a free silver activity in the electrolyte between $10^{-6}$ and $10^{-17}$.

25. The dosimeter of claim 15 wherein the silver complexing agent is $Na_4$ EDTA.

26. The dosimeter of claim 15 wherein the concentration of $Na_4$ EDTA is 1 M and the concentration of $AgNO_3$ is $7 \times 10^{-4}$ M.

27. A chemically integrating dosimeter for measuring sulfur dioxide gas in the atmosphere comprising:

a structural base, open on one side, for housing a solution;

an internal electrolyte solution containing bromide ion and mercuric bromide placed in the structural base so that upon absorption of $SO_2$ gas into the electrolyte a chemical reaction occurs within the electrolyte causing a change in bromide ion concentration;

a gas permeable, liquid impermeable gas permeation rate-controlling outer membrane with a permeation rate for $SO_2$ gas substantially lower than the diffusion rate of $SO_2$ gas in air, placed to cover the opening in the structural base;

a microporous hydrophobic inner membrane substantially more permeable to gases than the outer membrane, impermeable to the internal electrolyte, and interposed between the internal electrolyte solution and the outer membrane to prevent chemical attack on the outer membrane by the electrolyte and to prevent precipitate deposition from the electrolyte on the outer membrane;

means to seal the inner membrane and the outer membrane to the structural base; and means to measure the change in concentration of bromide ions $Br^-$ in the internal electrolyte.

28. The dosimeter of claim 27 wherein the outer membrane is silicone rubber.

29. The dosimeter of claim 27 wherein the outer membrane is silicone polycarbonate copolymer.

30. The dosimeter of claim 27 wherein the inner membrane is microporous polytetrafluoroethylene.

31. The dosimeter of claim 27 wherein the inner membrane is microporous polyvinylchloride.

32. The dosimeter of claim 27 wherein the inner membrane is microporous polyethylene.

33. The dosimeter of claim 27 wherein the inner membrane is microporous polyvinylfluoride.

34. The dosimeter of claim 27 wherein the inner membrane is polypropylene.

35. The dosimeter of claim 27 wherein the internal electrolyte contains an acetic acid buffer.

36. The dosimeter of claim 27 wherein the internal electrolyte contains dimethylformamide.

37. The dosimeter of claim 27 wherein the internal electrolyte solution is $1 \times 10^{-3}$ M mercuric bromide ($HgBr_2$) in $5 \times 10^{-3}$ M acetic acid buffer (HOAc/NaOAc) at pH 4.8 with 1% dimethylformamide.

38. Method for detecting sulfur dioxide gas by chemical integration comprising the steps of:

providing a gas permeable, liquid impermeable outer membrane in conjunction with a liquid impermeable microporous hydrophobic inner membrane, the latter with a gas permeation rate substantially greater than that of the outer membrane;

placing an internal electrolyte solution containing bromide ion and mercuric bromide in contact with the inner membrane;

allowing sulfur dioxide gas to diffuse through the outer membrane, through the inner membrane, and into the internal electrolyte where the outer membrane is a gas permeation rate controlling membrane, and the inner membrane is a protective membrane;

reacting the internal electrolyte with sulfur dioxide gas to completely absorb said gas and to alter the composition of the internal electrolyte; and measuring the change in the concentration of bromide ions in the electrolyte due to the entry of sulfur dioxide gas into the internal electrolyte, whereby the concentration of the gas is determined.

39. The method of claim 38 wherein the outer membrane is silicone rubber.

40. The method of claim 38 wherein the outer membrane is silicone polycarbonate copolymer.

41. The method of claim 38 wherein the inner membrane is microporous polytetrafluoroethylene.

42. The method of claim 38 wherein the inner membrane is microporous polyvinylchloride.

43. The method of claim 38 wherein the inner membrane is microporous polyvinylfluoride.

44. The method of claim 38 wherein the inner membrane is polypropylene.

45. The method of claim 38 wherein the internal electrolyte contains an acetic acid buffer.

46. The method of claim 38 wherein the internal electrolyte contains dimethylformamide.

47. The method of claim 38 wherein the internal electrolyte solution is $1 \times 10^{-3}$ M mercuric bromide ($HgBr_2$) in $5 \times 10^{-3}$ M acetic acid buffer (HOAc/NaOAc) at pH 4.8 with 1% dimethylformamide.

* * * * *